US006652701B1

(12) United States Patent
Boulanger (10) Patent No.: US 6,652,701 B1
(45) Date of Patent: Nov. 25, 2003

(54) ABSORBENT ARTICLE AND METHOD AND APPARATUS FOR MANUFACTURING SAME

(75) Inventor: Roger Boulanger, Sainte-Julie (CA)

(73) Assignee: Johnson & Johnson, Inc., Montreal (CA)

( * ) Notice: Subject to any disclaimer, the term of this patent is extended or adjusted under 35 U.S.C. 154(b) by 0 days.

(21) Appl. No.: 09/331,985

(22) PCT Filed: Dec. 30, 1997

(86) PCT No.: PCT/CA97/00994

§ 371 (c)(1),
(2), (4) Date: Sep. 7, 1999

(87) PCT Pub. No.: WO98/29070

PCT Pub. Date: Jul. 9, 1998

(30) Foreign Application Priority Data

Dec. 30, 1996 (CA) ............................................. 2194125

(51) Int. Cl.[7] .......................... A61F 13/15; B32B 31/00
(52) U.S. Cl. .................. 156/267; 604/385.04; 604/386; 156/264; 156/270; 156/271; 156/269
(58) Field of Search ............................ 604/387, 385.01, 604/385.04, 385.05, 386; 156/227, 256, 264, 259, 270, 271, 250, 269, 268, 267; 83/78–89

(56) References Cited

U.S. PATENT DOCUMENTS

| | | | | |
|---|---|---|---|---|
| 4,701,177 A | * | 10/1987 | Ellis et al. ................... | 604/385 |
| 4,862,574 A | * | 9/1989 | Seidy .......................... | 29/415 |
| 6,171,432 B1 | * | 1/2001 | Brisebois et al. ............ | 156/260 |

FOREIGN PATENT DOCUMENTS

| | | |
|---|---|---|
| EP | 0 280 998 B1 | 9/1988 |
| EP | 0 768 073 B1 | 4/1997 |
| FR | 2 209 520 | 7/1974 |
| WO | WO 96/21411 A1 | 7/1996 |
| WO | WO 97/27032 A1 | 7/1997 |

OTHER PUBLICATIONS

International Search Report—PCT Application No. PCT/CA 97/00994—dated May 22, 1998.

* cited by examiner

*Primary Examiner*—Weilun Lo
*Assistant Examiner*—Jacqueline F Stephens (57) ABSTRACT

A method of manufacturing sanitary absorbent articles suitable for placement within a crotch portion of an undergarment of a wearer, the absorbent article having a main body and a flap projecting laterally from a respective longitudinal side of the main body, the first flap having to longitudinal sides, each longitudinal side projecting laterally outward from the first longitudinal side of said main body intermediate the transverse sides of said main body. The method includes the steps of providing a web of at least one layer of continuous material, severing from the web a first article and a second article arranged with respect to the other wherein when the second article is rotated with respect to the first article such that the first longitudinal side of the main body of each of the articles faces the first longitudinal side of the main body of the other of the articles and such that the first transverse side of each of the articles is aligned with the second transverse side of the other of the articles, an imaginary line generally parallel to, and located in-between the longitudinal center-lines of each of the main bodies of each of the articles simultaneously intersects the first flap of each of the articles.

1 Claim, 4 Drawing Sheets

ABSORBENT ARTICLE AND METHOD AND APPARATUS FOR MANUFACTURING SAME

This application is a national stage, filed under 35 USC 371 of PCT application CA97/00994, filed Dec. 30, 1997.

FIELD OF THE INVENTION

The present invention relates to a sanitary absorbent article such a sanitary napkin, diaper, adult brief, incontinence pad and the like. More particularly, the invention relates to a novel sanitary absorbent article and to a component layer thereof that can be produced with less waste material generated, and to a method of and apparatus for the manufacture thereof. The invention also extends to a method and apparatus for manufacturing the novel absorbent article.

BACKGROUND OF THE INVENTION

The technology surrounding absorbent articles, particularly sanitary napkins, has undergone several advances over the past two decades. One of these advances was the addition of multi-functional flaps to the longitudinal sides of the napkin. When in use such flaps are folded over the sides of the wearer's undergarment and secured thereto. They thus more firmly secure the napkin to the undergarment, provide an increased absorptive area for bodily exudates, and help prevent the undergarment from becoming soiled. The flap concept has generally met with success in the marketplace, and napkins with flaps of various configurations and conformations are available to the consumer.

Such sanitary absorbent articles are ordinarily composed of several layers of various materials affixed together to form a laminated structure. They are generally manufactured in the following manner: A laminated web comprised of the materials forming each of the individual component layers of the final article is provided. At least one layer of material, and more likely several, is continuous throughout the web. The web is then sealed at various points and severed to form discrete articles.

Alternatively, although generally uncommon, each of the individual component layers which make up the article could be produced separately, through their severance from a continuous sheet of material of which the layer is formed. These various component layers could then be combined together (i.e. laminated) to form the article.

In either method, the articles or the component layers themselves (as the case may be) receive their shape as they are severed from the laminated web or the continuous material, respectively.

Figure 1:
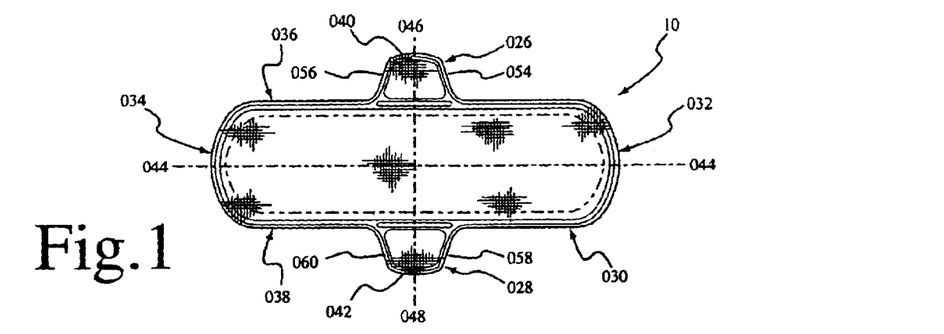
FIG. 1 illustrates a top elevational view of a sanitary absorbent article of the prior art.
Figure 2:
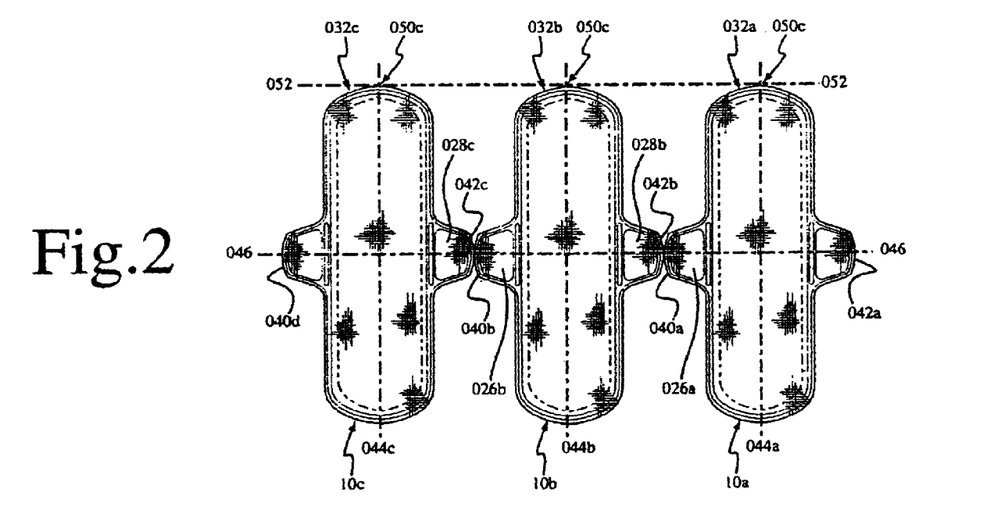
FIG. 2 illustrates a plurality of prior art absorbent articles, depicting the severing pattern employed for separating the absorbent articles from one another.

An example of a sanitary napkin and a severing pattern therefor currently employed in the art are illustrated in FIGS. 1 and 2, respectively, of the present specification. This severing pattern may be employed in either of the aforementioned methods for the manufacture of such articles. The article being produced by this pattern is symmetric about both imaginary longitudinal and transverse centre-lines. The transverse ends of successive articles are aligned and the longitudinal side of opposing flaps of successive articles are substantially in contact with one another. The shaded material is not used in the production of an article and is therefore discarded as waste. Depending on the shape of the item being manufactured, the amount of waste is substantial, which contributes to an increased manufacturing cost.

Heretofore it appears that manufacturers have sought to optimise the configuration and shape of the sanitary absorbent articles generally, and particularly the flaps, on the basis of characteristics present in the individual final product. In this respect wearer comfort, absorptive efficiency, and leakage prevention have generally been taken into consideration. While the cost of manufacturing is important, little attention has been paid to designing the individual articles with a view to reducing the amount of waste material produced during their mass-production by the methods described above. As such articles are mass-produced in significant amounts, a reduction in waste material would provide significant savings in the cost of manufacturing.

OBJECTS AND STATEMENT OF THE INVENTION

It is therefore an object of the present invention to provide an improved sanitary absorbent article with flaps, such as a sanitary napkin, or a component layer of a sanitary napkin, such as a cover layer, which has been designed so as to reduce the amount of waste material generated during the mass-production thereof.

It is a further object of the present invention to provide a method of production of such an absorbent article or a component layer. It is still a further object of the present invention to provide an apparatus for producing such an absorbent article or component layer.

In one aspect, as embodied and broadly described herein, the invention provides a plurality of component layers for use in sanitary absorbent articles, each component layer comprising:

(A) a main body, said main body having a first transverse side, a second transverse side, a first longitudinal side, a second longitudinal side, and an imaginary longitudinal centre-line;

(B) a first flap projecting laterally from the first longitudinal side of said main body, said first flap having two longitudinal sides, and said first flap being positioned with respect to said main body such that when
  (i) two of the component layers are placed longitudinal side by longitudinal side, and
  (ii) one of the component layers is rotated with respect to the other of the component layers such that the first longitudinal side of said main body of each of the component layers faces the first longitudinal side of said main body of the other of the component layers, and
  (iii) the first transverse side of said main body of each of the component layers is aligned with the second transverse side of said main body of the other of the component layers, and
  (iv) an imaginary line generally parallel to, and located in-between, the longitudinal centre-lines of each of said main bodies of each of the component layers simultaneously intersects said first flap of each of the component layers;
    one of the longitudinal sides of said first flap of one of the component layers is substantially in contact with one of the longitudinal sides of said first flap of the other of the component layers, and
    said first flaps of each of the component layers do not overlap.

In the present specification, the term "component layer of a laminated absorbent article" refers one of the discrete layers of which a laminated absorbent article is comprised as distinct from the other layers of which the same article is composed. For example, if the laminated absorbent article is a sanitary napkin, such component layer might be a fluid permeable cover layer, a fluid impervious barrier layer, a transfer layer or an absorbent core layer. A component layer need not be comprised of a single material, but may itself be a laminate or two or more materials otherwise combined to form an integral whole.

It is preferred that the main body of the component layer be generally rectangular in shape with rounded ends. When the component layer is of such a conformation, the first and second transverse sides are the shorter opposing sides and will generally have an arcuate shape. The first and second longitudinal sides are the longer opposing sides and will be straight or arcuate. Preferably, the longitudinal sides are in an hourglass shape wherein in a central portion of the article the cross-section is narrower than the cross-section at the transverse ends. It should be understood however that the shape of such sides is not essential to the invention, and thus the transverse or the longitudinal sides could be either arcuate or straight, or any combination thereof. Nor is it essential that the main body be generally rectangular, as component layers having main bodies in the shape of a square, parallelogram or any other polygon, or even that of an oval, hour-glass or dog-bone, are all within the scope of the present invention. Where such is the case (i.e. where the main body is not rectangular), the longitudinal sides of the layer will be considered to be those opposing sides of a greater relative length as compared with the other opposing sides of the main body. Where it is impossible to make such a determination, any opposing pair of sides may be considered to be the longitudinal sides, or at the limit, opposing portions of any two sides may be considered to be the longitudinal sides. In either case, the transverse sides are the pair of opposing sides which are intersected by the longitudinal centre-line of the component layer, as that line is defined below.

For most component layers, the longitudinal centre-line thereof is an imaginary line which extends along the longitudinal axis of the layer and bisects the layer into two identical or somewhat identical, yet not necessarily mirror-image, halves.

It is preferred that the flaps be of a generally trapezoidal shape with the base of the trapezoid being attached to the longitudinal side of the main body. In this manner, the flap will taper as it projects away from the main body, and the sides and top of the trapezoid will be generally straight and will form the longitudinal sides and lateral side of the flap respectively. It should expressly be understood, however, that such trapezoidal shape is not essential to the invention, and flaps of all shapes and sizes are included within the scope of the present invention. In such cases, the sides of the flaps generally parallel to the transverse sides of the component layer should be considered to be the longitudinal sides of the flap. Where the shape of the flaps is arcuate or other non-rectilinear shape, the portions of the side of the flap generally facing in the same direction as the transverse sides of the component layer should be considered to be the longitudinal sides of the flap.

It should be understood that the use of the word "flaps" in the present specification is intended to encompass extensions of the material of a component layer which directly form a flap or wing in the article into which the component layer is incorporated, and those which are indirectly used to form such a flap or wing. An example of an indirect formation would be situations where the extension is looped around and a portion thereof sealed against the barrier layer of the article. In such cases the remainder of the extension (i.e. the portion thereof from the barrier layer seal to the distal extremity) would form the flap or wing in the final article.

In the present context, the word "aligned" is used to indicate a position of a transverse side of one component layer relative to that of the other. Two transverse sides are aligned for the present purposes when an imaginary line connecting the point at which one transverse side in question is intersected by the longitudinal centre line of that layer, with the point at which the other transverse side in question is intersected by the longitudinal centre line of the other layer, is substantially perpendicular to the longitudinal centre-line of either layer. Two lines are substantially perpendicular if the angle between them at their point of intersection is not less than 70° (or more than 110°).

A line "generally parallel to the longitudinal centre-lines of the article" in the present specification is meant to include a line off from parallel with either one of the centre-lines by at most 20°.

In relation to a component layer of the present invention, the phrase "substantially in contact" is meant to indicate a situation where the two flaps in question are in physical contact with one another or where the distance between them is small as compared to the total width of the component layer (as measured from longitudinal side to longitudinal side along the transverse centre-line thereof. The transverse centre-line of a layer being an imaginary line in the plane of the layer which is perpendicular to the longitudinal centre-line). Preferably, in the case of a component layer for a sanitary napkin, this distance will not exceed ¼ of an inch (0.635 cm).

In a more preferred embodiment a component layer of the present invention further comprises a second flap projecting laterally from the second longitudinal side of said main body, said second flap having two longitudinal sides, and said second flap being positioned with respect to said main body such that when (i) two of the component layers are placed longitudinal side by longitudinal side, and (ii) one of the component layers is rotated with respect to the other of the component layers such that the second longitudinal side of said main body of each of the component layers faces the second longitudinal side of said main body of the other of the component layers, and (iii) the first transverse side of said main body of each of the component layers is aligned with the second transverse side of said main body of the other of the component layers, and (iv) an imaginary line generally parallel to, and located in-between, the longitudinal centre-lines of each of said main bodies of each of the component layers simultaneously intersects said second flap of each of the component layers;

one of the longitudinal sides of said second flap of one of said component layers is substantially in contact with one of the longitudinal sides of said second flap of the other of said component layers, and said second flaps of each of said component layers do not overlap.

As embodied and broadly described herein, the present invention further provides a plurality of sanitary absorbent articles, each article comprising:

(A) a main body, said main body having a first transverse side, a second transverse side, a first longitudinal side, a second longitudinal side, and an imaginary longitudinal centre-line;

(B) a first flap projecting laterally from the first longitudinal side of said main body, said first flap having two longitudinal sides, and said first flap being positioned with respect to said main body such that when
  (i) two of the articles are placed longitudinal side by longitudinal side, and
  (ii) one of the articles is rotated with respect to the other of the articles such that the first longitudinal side of said main body of each of the articles faces the first longitudinal side of said main body of the other of the articles, and
  (iii) the first transverse side of said main body of each of the articles is aligned with the second transverse side of said main body of the other of the articles, and
  (iv) an imaginary line generally parallel to, and located in-between, the longitudinal centre-lines of each of said main bodies of each of the articles simultaneously intersects said first flap of each of the articles;
    one of the longitudinal sides of said first flap of one of the articles is substantially in contact with one of the longitudinal sides of said first flap of the other of the articles, and
    said first flaps of each of the articles do not overlap.

Like terms used in the above description should be attributed the same meaning in the context of the present aspect as those previously described above in relation to component layers of the present invention.

In a more preferred embodiment each absorbent article of the present invention further comprises:
  (C) a second flap projecting laterally from the second longitudinal side of said main body, said second flap having two longitudinal sides, and said second flap being positioned with respect to said main body such that when
    (i) two of the articles are placed longitudinal side by longitudinal side, and
    (ii) one of the articles is rotated with respect to the other of said articles such that the second longitudinal side of said main body of each of the articles faces the second longitudinal side of said main body of the other of the articles, and
    (iii) the first transverse side of said main body of each of the articles is aligned with the second transverse side of said main body of the other of the articles, and
    (iv) an imaginary line generally parallel to, and located in-between, the longitudinal centre-lines of each of said main bodies of each of the articles simultaneously intersects said second flap of each of the articles;
      one of the longitudinal sides of said second flap of one of the articles is substantially in contact with one of the longitudinal sides of said second flap of the other of the articles, and
      said second flaps of each of the articles do not overlap.

In another aspect the invention provides a method of manufacturing a plurality of component layers for use in sanitary absorbent articles, each component layer comprising:
  (i) a main body, the main body having a first transverse side, a second transverse side, a first longitudinal side, a second longitudinal side, and a longitudinal centre-line; and
  (ii) a first flap projecting laterally from the first longitudinal side of the main body, the first flap having two longitudinal sides; comprising the steps of:
    (A) providing a continuous web of material;
    (B) severing said web to form a first component layer and a second component layer arranged one with respect to the other such that:
      (1) the second component layer is rotated with respect to the first component layer such that the first longitudinal side of the main body of one of the component layers faces the first longitudinal side of the main body of the other of the component layers, and
      (2) the first transverse side of one of the component layers is aligned with the second transverse side of the other of the component layers, and
      (3) an imaginary line generally parallel to, and located in-between, the longitudinal centre-lines of each of the main bodies of each of the component layers simultaneously intersects the first flap of each of the component layers.

The terms used to describe the component layer being manufactured by the present method should be given the same meaning as that of like terms set forth hereinabove in relation to the component layer itself.

It must be understood that for a proper understanding of these aspects of the invention (i.e. the methods), and those relating to the apparatus improvements described below, the evaluation of the positioning of the various component layers takes place after each layer has been severed (such that the layer in question exists as a discrete entity), but before it has been physically removed from the web of continuous material.

It will be appreciated that many conventional means known to those skilled in the art may be employed to sever the component layers from the web. The optimal means may vary depending on many factors including the material from which the layer is to be severed. In this respect, die-cutting will generally be the preferred method although all other conventional methods, such as laser or fluid-jet cutting for example, are within the scope of the present invention.

This method of manufacture of component layers from a continuous web of material will generate less wasted material than prior art techniques.

Preferably, the second component layer is severed from the web such that one of the longitudinal sides of the first flap of the second component layer is substantially in contact with one of the longitudinal sides of the first flap of the first component layer. In this context, the phrase "substantially in contact" is meant to indicate a situation where the distance between the two flaps in question is, at a minimum the clearance distance between layers required by the severing method being used in order to produce layers of the correct dimensions. This phrase also includes any greater distance which is small as compared with the total width of a component layer (as measured from longitudinal side to longitudinal side along the transverse centre-line thereof.) As an example, where die-cutting is the method of severance employed, the minimum clearance distance is generally in the order of 3/16 of an inch (0.4763 cm).

More preferably, the present invention provides a method of manufacturing a plurality of component layers for use in absorbent articles, each component layer further comprising:
  (iii) a second flap projecting laterally from the second longitudinal side of the main body, the second flap having two longitudinal sides;
further comprising the step of:
  (C) severing from the web a third component layer arranged with respect to the second component layer such that:
    (1) the third component layer is rotated with respect to the second component layer such that the second longitudinal side of the main body of the second component layer faces the second longitudinal side of the main body of the third component layer, and (2) the first transverse side of the second component layer is aligned with the second transverse side of the third component layer, and (3) the first transverse side of the third component layer is aligned with the second transverse side of the second component layer, and (4) an imaginary line generally parallel to, and located in-between, the longitudinal centre-lines of the main bodies of each of the second and third component layers simultaneously intersects the second flap of the second component layer and the second flap of the third component layer.

Most preferably, in order to minimize the amount of waste material generated, the third component layer is severed from the web such that one of the longitudinal sides of the second flap of the third component layer is substantially in contact with one of the longitudinal sides of the second flap of the second component layer.

As embodied and broadly described herein, the present invention also provides a method of manufacturing a plurality of sanitary absorbent articles, each sanitary absorbent article comprising:

(i) a main body, the main body having a first transverse side, a second transverse side, a first longitudinal side, a second longitudinal side, and a longitudinal centre-line; and (ii) a first flap projecting laterally from the first longitudinal side of the main body, the first flap having two longitudinal sides;

comprising the steps of:

(A) providing a web having at least one layer of continuous material;

(B) severing said web to form a first article and a second article arranged one with respect to the other such that:

(1) the second article is rotated with respect to the first article such that the first longitudinal side of the main body of one of the articles faces the first longitudinal side of the main body of the other of said articles, and (2) the first transverse side of one of the articles is aligned with the second transverse side of the other of the articles, and (3) an imaginary line generally parallel to, and located in-between, the longitudinal centre-lines of each of the main bodies of each of the articles simultaneously intersects the first flap of each of the articles.

Preferably, the present invention also provides a method of manufacturing a sanitary absorbent article wherein the second article is severed from the web such that one of the longitudinal sides of the first flap of the second article is substantially in contact with one of the longitudinal sides of the first flap of the first article.

More preferably, the present invention provides a method of manufacturing a plurality of sanitary absorbent articles, each sanitary absorbent article further comprising:

(iii) a second flap projecting laterally from the second longitudinal side of the main body, the second flap having two longitudinal sides;

further comprising the steps of:

(C) severing from the web a third article arranged with respect to the second article such that:

(1) the third article-is rotated with respect to the second article such that the second longitudinal side of the main body of the second article faces the second longitudinal side of the main body of the third article, and (2) the first transverse side of the second article is aligned with the second transverse side of the third article, and (3) the first transverse side of the third article is aligned with the second transverse side of the second article, and (4) a imaginary line generally parallel to, located in-between, the longitudinal centre-lines of each of the main bodies of each of the second and third articles simultaneously intersects the second flap of the second article and the second flap of the third article.

Most preferably the present invention provides, a method of manufacturing a plurality of sanitary absorbent articles, wherein the third article is severed from the web such that one of the longitudinal sides of the second flap of the third article is substantially in contact with one of the longitudinal sides of the second flap of the second article.

Like terms used in the description of a method of manufacture of an absorbent article in respect of this aspect of the present invention should be attributed a similar meaning as with the terms used to describe the method of manufacture of a component layer of this aspect of the present invention.

As embodied and broadly described herein, in another aspect, the present invention further provides in an apparatus for the manufacture of a plurality of component layers for use in sanitary absorbent articles, each component layer comprising:

(i) a main body, the main body having a first transverse side, a second transverse side, a first longitudinal side, a second longitudinal side, and a longitudinal centre-line;

(ii) a first flap projecting from the first longitudinal side of the main body, the first flap having two longitudinal sides;

the improvement comprising a cutter providing for the severance of a first component layer and a second component layer from a continuous web of material, the first component layer and the second component layer arranged one with respect to the other such that:

(A) the second component layer is rotated with respect to the first component layer such that the first longitudinal side of the main body of one of the component layers faces the first longitudinal side of the main body of the other of said component layers, and (B) the first transverse side of the first component layers is aligned with the second transverse side of the second component layer, and (C) the first transverse side of the second component layers is aligned with the second transverse side of the first component layer, and (D) an imaginary line generally parallel to, and located in-between, the longitudinal centre-lines of each of the main bodies of each of the component layers simultaneously intersects the first flap of each of the component layers.

Like terms used in the description of the component layers and their relationship to one another with respect to the present aspect of the invention should, to the extent not varied hereinbelow, be attributed a similar meaning to as described hereinabove with respect to other aspects of the invention.

The term "cutter" is employed in the present context to denote any device capable of severing a discrete item from a continuous web of material. All conventional cutters known to those skilled in the art are within the scope of this aspect of the present invention. In this respect, such a cutter may include a die, a blade or other cutting-edge, a laser, or a fluid-jet.

Advantageously, the cutter is further capable of severing the first component layer and the second component layer from the continuous web of material such that one of the longitudinal sides of the first flap of the first component layer is substantially in contact with one of the longitudinal sides of the second flap of the second component layer.

Preferably, as embodied and described herein, the present invention further provides in an apparatus for the manufacture of a plurality of component layers for use in sanitary absorbent articles, each component layer further comprising:

(iii) a second flap projecting from the second longitudinal side of the main body, the second flap having two longitudinal sides;

the improvement wherein said cutter further provides for the severance of a third component layer from the continuous web of material arranged with respect to the second component layer such that:

(A) the third component layer is rotated with respect to the second component layer such that the second longitudinal side of the main body of the second component layer faces the second longitudinal side of the main body of the third component layer, and (B) the first transverse side of the second component layer is aligned with the second transverse side of the-third component layer, and (C) the first transverse side of the third component layer is aligned with the second transverse side of the second component layer, and (D) an imaginary line generally parallel to, and located in-between, the longitudinal centre-lines of each of the main bodies of the second and of the third component layers simultaneously intersects the second flap of the second component layer and the second flap of the third component layer.

Advantageously, said cutter is further capable of severing the first component layer and the second component layer such that one of the longitudinal sides of the first flap of the first component layer is substantially in contact with one of the longitudinal sides of the first flap of the second component layer.

Of a similar advantage, said cutter is further capable of severing the second component layer and the third component layer such one of the longitudinal sides of the second flap of the second component layers is substantially in contact with one of the longitudinal sides of the second flap of the third component layer.

As embodied and broadly described herein, the present invention also provides in an apparatus for the manufacture of a plurality of sanitary absorbent articles, each sanitary absorbent article comprising:

(i) a main body, the main body having a first transverse side, a second transverse side, a first longitudinal side, a second longitudinal side, and a longitudinal centre-line;

(ii) a first flap projecting from the first longitudinal side of the main body, the first flap having two longitudinal sides;

the improvement comprising a cutter providing for the severance of a first article and a second article from a continuous web of material, the first and second article being arranged one with respect to the other such that:

(A) the second article is rotated with respect to the first article such that the first longitudinal side of the main body of each of the articles faces the first longitudinal side of the main body of the other of said articles, and (B) the first transverse side of the first article is aligned with the second transverse side of the second article, and (C) the first transverse side of the second article is aligned with the second transverse side of the first article, and (D) an imaginary line generally parallel to, and located in-between, the longitudinal centre-lines of each of the main bodies of each of the articles simultaneously intersects the first flap of each of the articles.

Advantageously, said cutter is further capable of severing the first article and the second article from the continuous web of material such that one of the longitudinal sides of the first flap of the first article is substantially in contact with one of the longitudinal sides of the second flap of the second article.

Preferably, as embodied and broadly described herein the present aspect of the present invention further provides in an apparatus for the manufacture of a plurality of sanitary absorbent articles, each sanitary absorbent article further comprising:

(iii) a second flap projecting from the second longitudinal side of the main body, the second flap having two longitudinal sides;

the improvement wherein said cutter further provides for the severance of a third article from the continuous web of material arranged with respect to the second article such that:

(A) the third article is rotated with respect to the second article such that the second longitudinal side of the main body of the second article faces the second longitudinal side of the main body of the third article, and (B) the first transverse side of the second article is aligned with the second transverse side of the third article, and (C) the first transverse side of the third article is aligned with the second transverse side of the second article, and (D) an imaginary line generally parallel to, and located in-between, the longitudinal centre-lines of each of the main bodies of each of the second and third sanitary absorbent articles simultaneously intersects the second flap of the second article and the second flap of the third article.

Advantageously, said cutter is further capable of severing the first article and the second article such that one of the longitudinal sides of the first flap of the first article is substantially in contact with one of the longitudinal sides of the first flap of the second article.

Of a similar advantage, said cutter is further capable of severing the second article and the third article such one of the longitudinal sides of the second flap of the second articles is substantially in contact with one of the longitudinal sides of the second flap of the third article.

In still another aspect, as embodied and broadly described herein, the present invention provides a method of manufacturing a plurality of component layers for use in sanitary absorbent articles, each component layer comprising:

(i) a main body, the main body having a first transverse side, a second transverse side, a first longitudinal side, a second longitudinal side, and a longitudinal centre-line;
(ii) a first flap projecting from the first longitudinal side of the main body;
(iii) a second flap projecting from the second longitudinal said of the main body; and
(iv) each of the flaps having a first longitudinal side, a second longitudinal side, and a lateral side;
(v) said flaps being located substantially at midpoint between said transverse sides; comprising the steps of:
(A) providing a web of continuous material;
(B) severing said web to form a first component layer and a second component layer arranged one with relation to the other such that:
(1) at least a portion of the first longitudinal side of the main body of the first component layer faces at least a portion of the second longitudinal side of the main body of the second component layer, and
(2) an imaginary line generally parallel to, and located in-between, the longitudinal centre-lines of each of the main bodies of each of the component layers simultaneously intersects the first flap of the first component layer and the second flap of the second component layer.

It will be appreciated that this aspect of the present invention is similar to the method previously described above. It differs, however, in that the present method allows for the production of component layers currently employed in the art that are symmetric about an imaginary transverse centre-line (such as the article illustrated in FIG. 1). Alternative component layers manufactured according to the present method need not be rotated.

Preferably, the second component layer is severed from the continuous web of material such that the first transverse side of the first component layer and the first transverse side of the second component layer are non-aligned. In this context the term "non-aligned" is used to indicate a situation where the angle formed between the longitudinal centre-line of the first component layer and the line connecting the point of intersection of the longitudinal centre-line of that layer with a transverse side thereof and the corresponding point on the second component layer is not 90°.

More preferably, the second component layer is severed from the web of continuous material such that the first longitudinal side of the first flap of the first component layer is substantially in contact with the second longitudinal side of the second flap of the second component layer. The term "substantially in contact" in this context has the same meaning as that of the previous method aspect of the present invention described hereinabove.

Most preferably, the second component layer is severed from the web of continuous material such that the lateral side of the first flap of the first component layer is substantially in contact with the second longitudinal side of the main body of the second component layer.

Alternatively, the second component layer is severed from the continuous web-of material-such that at least a portion of one of the longitudinal sides of the second flap of the second component layer faces at least a portion of one of the transverse sides of the first component layer.

Advantageously, the second component layer is severed from the continuous web of material such that at least a portion of one of the longitudinal sides of the second flap of the second component layer is substantially in contact with one of the transverse sides of the first component layer.

More advantageously, the second component layer is severed from the continuous web of material such that at least a portion of the first longitudinal side of the main body of the first component layer is substantially in contact with at least a portion of the second longitudinal side of the main body of the second component layer.

In another aspect, as embodied and broadly described herein, the present invention provides a method of manufacturing a plurality of sanitary absorbent articles, each sanitary absorbent article comprising:
(i) a main body, the main body having a first transverse side, a second transverse side, a first longitudinal side, a second longitudinal side, and a longitudinal centre-line;
(ii) a first flap projecting from the first longitudinal side of the main body;
(iii) a second flap projecting from the second longitudinal said of the main body; and
(iv) each of the flaps having a first longitudinal side, a second longitudinal side, and a lateral side;
(v) said flaps being located substantially at mid point between said transverse sides;
comprising the steps of:
(A) providing a web of continuous material;
(B) severing said web to form a first sanitary absorbent article and a second sanitary absorbent article arranged one with respect to the other such that:
(1) at least a portion of the first longitudinal side of the main body of the first article faces at least a portion of the second longitudinal side of the main body of the second article, and
(2) an imaginary line generally parallel to, and located in-between, the longitudinal centre-lines of each of the main bodies of each of the articles simultaneously intersects the first flap of the first article and the second flap of the second article.

Preferably, the second article is severed from the continuous web of material such that the first transverse side of the first article and the first transverse side of the second article are non-aligned.

More preferably, the second article is severed from the web of continuous material such that the first longitudinal side of the first flap of the first article is substantially in contact with the second longitudinal side of the second flap of the second article.

Most preferably, the second component layer is severed from the web of continuous material such that the lateral side of the first flap of the first component layer is substantially in contact with the second longitudinal side of the main body of the second component layer.

In this aspect of the present invention the terms used have a meaning similar to that described previously hereinabove in relation to a method of manufacture of a component layer for use in a sanitary absorbent article.

In yet another aspect, as embodied and broadly described herein, the present invention further provides in an apparatus for the manufacture of a plurality of component layers for use in sanitary absorbent articles, each component layer comprising:
(i) a main body, the main body having a first transverse side, a second transverse side, a first longitudinal side, a second longitudinal side, and a longitudinal centre-line;
(ii) a first flap projecting from the first longitudinal side of the main body;
(iii) a second flap projecting from the second longitudinal said of the main body; and (iv) each of the flaps having a first longitudinal side, a second longitudinal side, and a lateral side;

(v) said flaps being located substantially at mid point between said transverse sides;

the improvement comprising a cutter providing for the severance of a first component layer and a second component layer from a continuous web of material, the first component layer and the second component layer being arranged one with respect to the other such that:

(A) at least a portion of the first longitudinal side of the main body of the first component layer faces at least a portion of the second longitudinal side of the main body of the second component layer, and (B) an imaginary line generally parallel to, and located in-between, the longitudinal centre-lines of each of the main bodies of each of the component layers simultaneously intersects the first flap of the first component layer and the second flap of the second component layer.

Preferably, said cutter is further capable of severing the second component layer from the continuous web of material such that the first transverse side of the first component layer and the first transverse side of the second component layer are non-aligned.

More preferably, said cutter is further capable of severing the second component layer from the continuous web of material such that the first longitudinal side of the first flap of the first component layer is substantially in contact with the second longitudinal side of the second flap of the second component layer.

Most preferably, said cutter is further capable of severing the second component layer from the web of continuous material such that the lateral side of the first flap of the first component layer is substantially in contact with the second longitudinal side of the main body of the second component layer.

In another aspect, as embodied and broadly described herein, the present invention provides in an apparatus for the manufacture of a plurality of sanitary absorbent articles, each article comprising:

(i) a main body, the main body having a first transverse side, a second transverse side, a first longitudinal side, a second longitudinal side, and a longitudinal centre-line;

(ii) a first flap projecting from the first longitudinal side of the main body;

(iii) a second flap projecting from the second longitudinal said of the main body; and (iv) each of the flaps having a first longitudinal side, a second longitudinal side, and a lateral side;

(v) said flaps being located at mid point between said transverse sides;

the improvement comprising a cutter providing for the severance of a first article and a second article from a continuous web of material, the first and second arranged one with respect to the other such that:

(A) at least a portion of the first longitudinal side of the main body of the first article faces at least a portion of the second longitudinal side of the main body of the second article, and (B) an imaginary line generally parallel to, and located in-between, the longitudinal centre-lines of each of the main bodies of each of the articles simultaneously intersects the first flap of the first article and the second flap of the second article.

Preferably, said cutter is further capable of severing the second article from the continuous web of material such that the first transverse side of the first article and the first transverse side of the second article are non-aligned.

More preferably, said cutter is further capable of severing the second article from the continuous web of material such that the first longitudinal side of the first flap of the first article is substantially in contact with the second longitudinal side of the second flap of the second article.

Most preferably, said cutter is further capable of severing the second article from the web of continuous material such that the lateral side of the first flap of the first article is substantially in contact with the second longitudinal side of the main body of the second article.

In this aspect of the present invention the terms used have a meaning similar to that described previously hereinabove in relation to a apparatus for the manufacture of a component layer for use in a sanitary absorbent article.

Other objects and features of the invention will become apparent by reference to the following specification and the drawings.

BRIEF DESCRIPTION OF THE DRAWINGS

A detailed description of the preferred embodiments of the present invention is provided hereinbelow with reference to the following drawings, in which.

In the drawings, preferred embodiments of the invention are illustrated by way of example. It is to be expressly understood that the description and drawings are only for the purposes of illustration and as an aid to understanding, and are not intended as a definition of the limits of the invention.

DETAILED DESCRIPTION OF THE PREFERRED EMBODIMENTS

Figure 3:
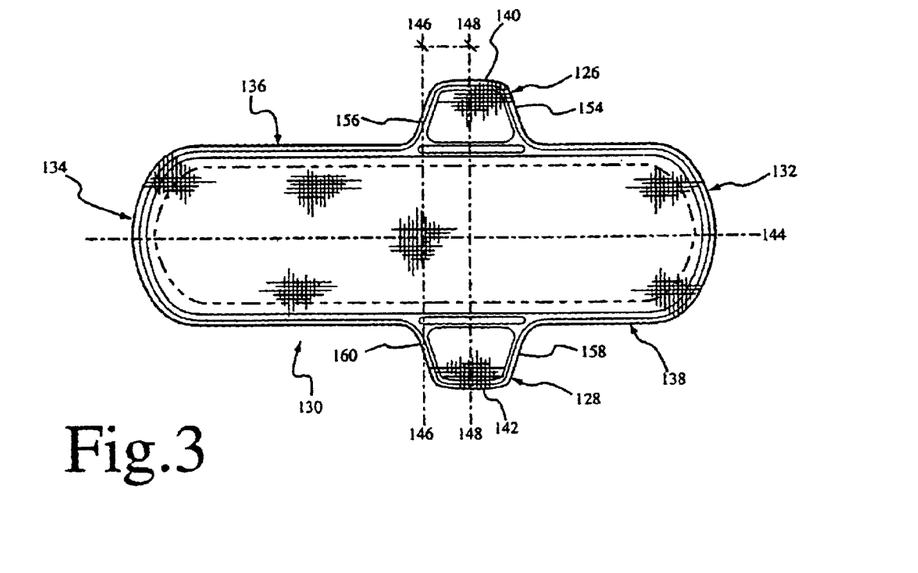
FIG. 3 illustrates a top elevational view of a sanitary absorbent article of the present invention.
Figure 3A:
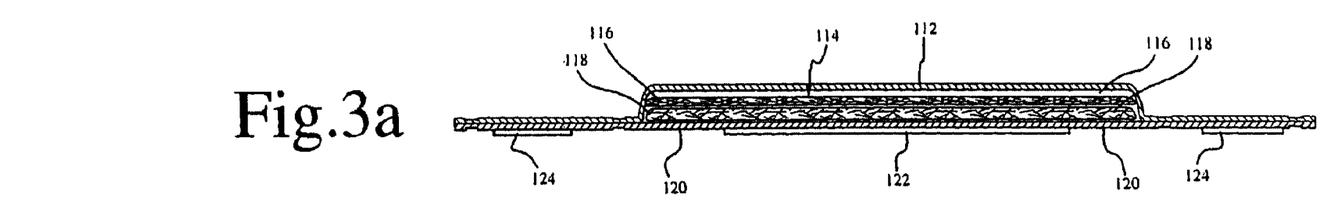
FIG. 3a is a cross-sectional view of the napkin shown in FIG. 3.
Figure 4:
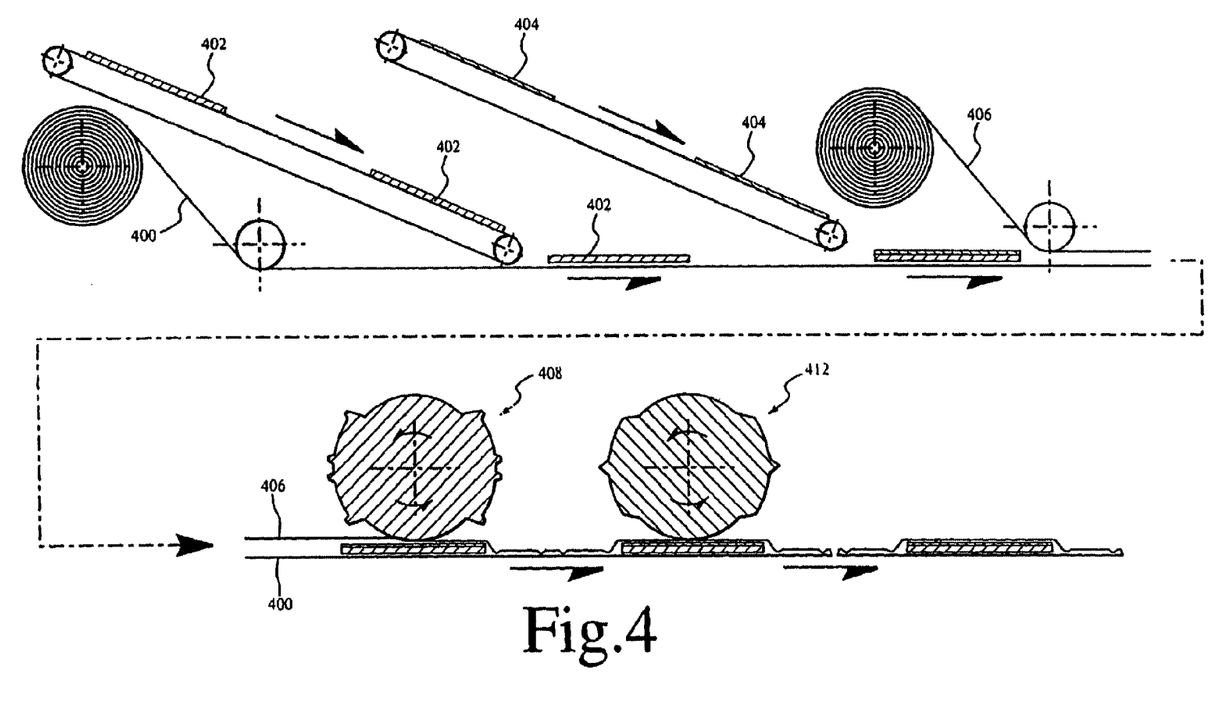
FIG. 4 schematically illustrates the process for manufacturing absorbent articles in accordance with the present invention.

In FIG. 3 of the drawings there is illustrated a sanitary napkin with flaps, designated comprehensively by the reference numeral 110, having a flap configuration of the present invention. Referring to FIG. 3a, the napkin is of a laminated construction and preferably comprises a fluid-permeable cover layer 112, an absorbent system 114, a fluid-impervious barrier layer 120, and adhesive strips 122 and 124.

Cover Layer

The cover layer 112 may be a relatively low density, bulky, high-loft non-woven web material. The cover layer 112 may be composed of only one type of fibre, such as polyester or polypropylene or it may be composed of bi-component or conjugate fibres having a low melting point component and a high melting point component. The fibres may be selected from a variety of natural and synthetic materials such as nylon, polyester, rayon (in combination with other fibres), cotton acrylic fibre and the like and combinations thereof.

Bi-component fibres may be made up of a polyester core and a polyethylene sheath. The use of appropriate bi-component materials results in a fusible non-woven fabric. Examples of such fusible fabrics are described in U.S. Pat. No. 4,555,430 issued Nov. 26, 1985 to Mays. Using a fusible fabric increases the ease with which the cover layer may be mounted to the adjacent transfer layer and/or to the barrier layer.

The cover layer 112 preferably has a relatively high degree of wettability, although the individual fibres comprising the cover may not be particularly hydrophilic. The cover material should also contain a great number of relatively large pores. This is because the cover layer 112 is intended to absorb body fluid rapidly and transport it away from the body and the point of deposition. Preferably, the fibres which make up the cover layer 112 should not loose their physical properties when they are wetted, in other words they should not collapse or loose their resiliency when subjected to water or body fluid. The cover layer 112 may be treated to allow fluid to pass through it readily. The cover layer 112 also functions to transfer the fluid quickly to the other layers of the absorbent structure 114. Thus, the cover layer 112 is preferably wettable, hydrophilic and porous. When composed of synthetic hydrophobic fibres such as polyester or bi-component fibres, the cover layer 112 may be treated with a surfactant to impart the desired degree of wettability.

Most preferably, the cover layer 112 is made of polymer film having large pores. Because of such high porosity, the film accomplishes the function of quickly transferring body fluid to the inner layers of the absorbent system. Apertured co-extruded films such as RETICULON™ brand, for example, described in U.S. Pat. No. 4,690,679 are useful as cover layers in the absorbent structures of this invention.

The cover layer 112 may be embossed to the remainder of the absorbent system 114 in order to aid in promoting hydrophilicity by fusing the cover to the next layer.

Absorbent System—Transfer Layer

Adjacent to the cover layer 112 on its inner side and bonded to the cover layer 112 is a fluid transfer layer 116 that forms part of the absorbent system 114. The transfer layer 116 provides the means of receiving body fluid from the cover layer 112 and holding it until the highly-dense absorbent core has an opportunity to absorb the fluid.

The transfer layer 116 is, preferably, more dense than and has a larger proportion of smaller pores than the cover layer 112. These attributes allow the transfer layer 116 to contain body fluid and hold it away from the outer side of the cover layer 112, thereby preventing the fluid from re-wetting the cover layer 112 and its surface. However, the transfer layer is, preferably, not so dense as to prevent the passage of the fluid through the layer into the absorbent core.

The transfer layer 116 may be composed of fibrous materials, such as wood pulp, polyester, rayon, flexible foam, or the like, or combinations thereof. The transfer layer 116 may also comprise thermoplastic fibres for the purpose of stabilizing the layer and maintaining its structural integrity. The transfer layer 116 may be treated with surfactant on one or both sides in order to increase its wettability, although generally the transfer layer 116 is relatively hydrophilic and may not require treatment. The transfer layer 116 is preferably bonded on both sides to the adjacent layers, i.e. the cover layer 112 and the absorbent core 118.

Absorbent System—Absorbent Core

Immediately adjacent to and bonded to the transfer layer 116 is the absorbent core 118. The absorbent core 118 is preferably a highly dense layer having a fine porosity. It has a large liquid holding capacity and it is extremely retentive. Most preferably, the absorbent core 118 is composed of compressed sphagnum moss material. More specifically, the sphagnum moss is formed as a board by air or wet laying and calendering to obtain a relatively thin, i.e. from about 0.01 to 0.10 inch (0.0254 cm to 0.254 cm) thick, relatively dense, i.e. from about 0.2 to 1.0 $g/cm^3$ sheet like structure. The structure may include a layer of Kraft tissue laminated on one or both surfaces of the sphagnum moss layer. Preferably, a fibrous component is admixed with the sphagnum moss material. The fibrous component is suitably a natural or synthetic textile fibre such as rayon, polyester, nylon, acrylic or the like, having a length of from about 0.25 to 1.5 inches (0.635 cm to 3.81 cm) and a denier of from about 1.0 to 5. The fibrous component may be present in an amount from about 2 to 20% by weight, most preferably from 4 to 8%. The absorbent core 118 may also comprise other components such as wood pulp, synthetic wood pulp, thermomecanical pulp, mechanically ground pulp, polymers; surfactants, superabsorbents and the like.

In an alternative embodiment the absorbent system 114 includes a single layer of pulp fluff material (the transfer layer is omitted). The absorbent core 116 preferably comprises a pulp fluff material and may optionally include other absorbent materials or non-absorbent materials which aid in stabilizing the absorbent structure such as conjugate fibres, fusible fibres, binders, sphagnum peat moss particles, superabsorbents, and the like and combinations thereof. and may optionally include other absorbent materials or non-absorbent materials which aid in stabilizing the absorbent structure such as conjugate fibres, fusible fibres, binders, sphagnum peat moss particles, superabsorbents, and the like and combinations thereof.

Barrier Layer

Underlying the absorbent system 114 is a barrier layer 120 comprising liquid-impervious film material so as to prevent liquid that is entrapped in the absorbent core from egressing the sanitary napkin and staining the wearer's undergarment. Most preferably, the barrier layer 120 is made of polymeric film, such as polyethylene which is both inexpensive and readily available. The polyethylene is capable of fully blocking the passage of liquid or gas that may emanate from the absorbent system 114. In a variant, breathable films may be used that allow passage of gases while blocking liquid.

The cover layer 112 and the barrier layer 120 are joined along their marginal portions so as to form an enclosure that maintains the absorbent system 114 captive. The joint may be made by means of adhesives, heat-bonding, ultrasonic bonding, radio frequency sealing, mechanical crimping, and the like and combinations thereof. The peripheral seal line is shown in FIG. 3 by the reference numeral 121.

Adhesive Strips

To retain the sanitary napkin 110 to the wearer's underpants, adhesive zones 122 and 124 are provided on the barrier layer 120. The adhesive zones 124, located over the flaps 126 and 128, bond the flaps to the garment facing surface of the wearer's underpants, while the adhesive zone 122 serves to retain the sanitary napkin 110 to the body facing surface of the underpants.

Flaps

The flaps 126 and 128 are designed to be folded over the side edges of the wearer's underpants in the crotch portion and to be fastened to the garment facing surface of the underpants. The flaps 126 and 128 aid in securing the sanitary napkin 110 in place on the wearer's underpants, and in maintaining the structural integrity of the sanitary napkin 110 by providing a "spring-back" action during body movements of the wearer. The overall effect of the flaps 126 and 128 is to fasten and keep the sanitary napkin 110 in an optimal exposed shape to provide the maximum fluid-absorbing surface, whereby reducing the incidence of failure.

Flap Configuration—Prior Art

In FIG. 1 there is illustrated a sanitary napkin 010 with flap configuration of the prior art. Such a napkin is comprised of a main body 030 having a first transverse side 032, an opposing second transverse side 034, a first longitudinal side 036, and an opposing second longitudinal side 038. A first flap 026 and a second flap 028 project laterally from the main body 030 from the first longitudinal side 036 and the second longitudinal side 038, respectively. The flaps 026 and 028 are in the shape of a bilaterally symmetrical trapezoid, with the base being located at the longitudinal side of the article. The top of the trapezoid forms the lateral side 040 and 042 of each flap 026 and 028, respectively.

The contour of the sanitary napkin 010 is symmetric about both an imaginary centre-line 044 extending longitudinally down the sanitary napkin and an imaginary centre-line 046 extending transversely across the sanitary napkin 010. Thus, there exists a line 048 which simultaneously symmetrically bisects the flaps 026 and 028, and that line 048 is collinear with the transverse centre-line 046 of the napkin 010.

In FIG. 2 there is illustrated a cutting pattern employed in the prior art to manufacture the napkin depicted in FIG. 1 from a web of at least one layer of continuous material. In such pattern, like transverse sides of successive napkins are aligned, i.e. the points of intersection 050a, 050b, 050c of the transverse side 032a, 032b, 032c of each napkin with the longitudinal centre-line 044a, 044b, 044c of the napkin are collinear, that line 052 is parallel to the transverse centre-line 046 of the article 010, and that line 052 is perpendicular to the longitudinal centre-lines 044a, 044b, 044c of the napkins. The lateral sides of opposing flaps of successive articles face one another (e.g. the lateral side 040a of the first flap 026a of the first article 010a faces the lateral side 042b of the second flap 028b of the second article 010b). Such opposing lateral sides 040a and 042b are substantially in contact in that the distance between them within the pattern is the minimum clearance distance dictated by the die being used to sever them from the web.

The shaded area in between is not used to produce a napkin from the web of material and must be discarded as waste during the manufacturing process.

Flap Configuration—Present Invention

Referring to FIG. 3, a sanitary napkin 110 having a flap configuration of the present invention is comprised of a main body 130 having a first transverse side 132 and an opposing second transverse side 134. Each transverse side is arcuate in shape with no particular curvature being essential to the present invention. The sanitary napkin 110 further has a first longitudinal side 136 and an opposing second longitudinal side 138, each being generally straight. The shape of the napkin 110 when viewed from above, as shown in FIG. 3, is nearly rectangular.

A first flap 126 and a second flap 128 project laterally from the main body 130 from the first longitudinal side 136 and second longitudinal side 138, respectively. Each of these flaps 126 and 128 is in the shape of a bilaterally symmetrical trapezoid, with the base being located at the longitudinal side of the article. The first flap 126 has a first longitudinal side 154 and a second longitudinal side 156 formed of the sides of the trapezoid, and a lateral side 140 formed of the top of the trapezoid. Similarly, the second flap 128 has a first longitudinal side 158 and a second longitudinal side 160 formed of the sides of the trapezoid, and a lateral side 142 formed of the top of the trapezoid. The first longitudinal side 154 of the first flap 126 and the first longitudinal side 158 of the second flap 128 each face in the same direction as does the first transverse side 132 of the main body 130 of the napkin 110. In the same respect, the second longitudinal side 156 of the first flap 126 and the second longitudinal side 160 of the second flap 128 face in the same direction as does the second transverse side 134 of the main body 130 of the napkin 110.

The contour of the sanitary napkin 110 is symmetric about an imaginary centre-line 144 extending longitudinally down the sanitary napkin 110. A single line 148 simultaneously symmetrically bisects both the first flap 126 and the second flap 128. A second centre-line 146 extends transversely across the sanitary napkin 110, from which the flaps 126 and 128 are offset. By offset it is meant that the line 148 which symmetrically bisects the flaps is not collinear with the transverse centre-line 146 of the napkin 110. The amount by which the flaps 126 and 128 are offset is described below in relation to the cutting pattern for the present napkin.

Figure 5:
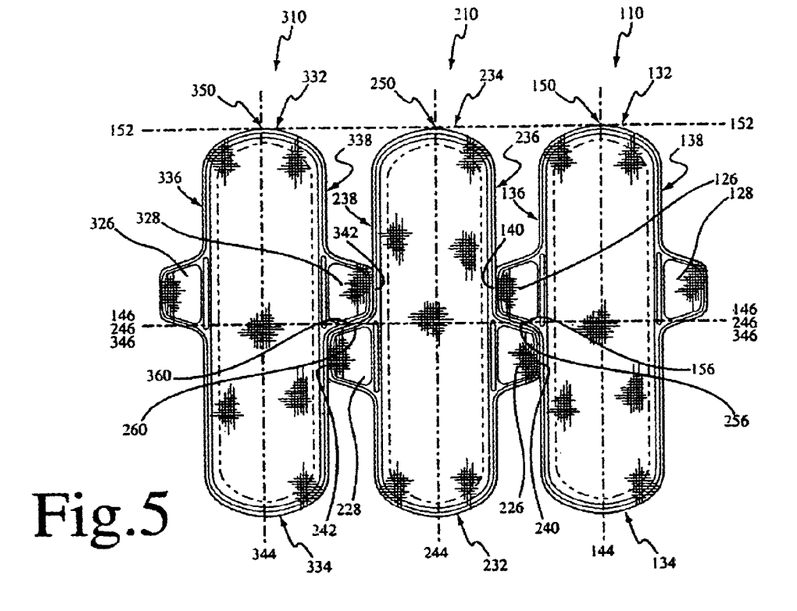
FIG. 5 illustrates a plurality of absorbent articles, depicting the severing pattern of the present invention employed for separating the absorbent articles from one another.

In FIG. 5 there is illustrated a cutting pattern of the present invention to be employed in the manufacture of sanitary napkins of the present invention from a web of a least one continuous material. In such a pattern successive napkins 110, 210, 310 are positioned side-by-side, and are rotated. The first transverse side 132 of the first napkin 110, the second transverse side 234 of the second napkin 210, and the first transverse side 332 of the third napkin 310 all face in a similar direction. Similarly, the second transverse side 134 of the first napkin 110, the first transverse side 232 of the second napkin 210, and the second transverse side 334 of the third napkin 310 all face in the same direction. The alternating sides of successive articles are aligned within the pattern, i.e. the points of intersection 150, 250, 350 of these transverse sides 132, 234, 332 (respectively) of these napkins 110, 210, 310 with their longitudinal centre-lines 144, 244, 344 (respectively) are collinear, the line 152 formed by connecting such points 150, 250, 350 is parallel to the transverse centre-lines 146, 246, 346 of the napkins, and that line 152 is perpendicular to the longitudinal centre-line 144, 244, 344 of the napkins.

Further, in the pattern illustrated in FIG. 5, like longitudinal sides of successive articles face one another. Thus, the first longitudinal side 136 of the first napkin 110 faces the first longitudinal 236 of the second napkin 210, and the second longitudinal side 238 of the second napkin 210 faces the second longitudinal side 338 of the third napkin 310, and so on.

The first flap 126, 226, 326 and the second flap 128, 228, 328 of the napkin 110, 210, 310 are positioned with respect to the main body 130, 230, 330 (i.e. are offset from the transverse centre-line 146, 246, 346) such that like longitudinal sides of like flaps of successive napkins are substantially in contact with one another. In FIG. 5, the second longitudinal side 156 of the first flap 126 of the first napkin 110 is in complete contact with the second longitudinal side 256 of the first flap 226 of the second napkin 210. Similarly, the second longitudinal side 260 of the second flap 228 of the second napkin 210 is in complete contact with the second longitudinal side 360 of the second flap 328 of the third napkin 310.

When such flaps are in complete contact, the lateral sides of the flaps will be substantially in contact with the longitudinal side of the facing napkin. Thus, as is shown, the lateral side 140 of the first flap 126 of the first napkin 110 is in contact with first longitudinal side 236 of the main body 230 of the second napkin 230 and the lateral side 240 of the first flap 226 of the second napkin 210 is in contact with the first longitudinal side 136 of the main body 130 of the first napkin 110. Similarly, the lateral side 242 of the second flap 228 of the second napkin 210 is in contact with the second longitudinal side 338 of the main body 330 of the third napkin 310, and the lateral side 342 of the second flap 328 of the third napkin 310 is in contact with the second longitudinal side 238 of the main body 230 of the second napkin 210.

The shaded area in between successive napkins is not used in the manufacture of any napkin and must be discarded as waste. By positioning the flaps of the napkin in accordance with the present invention, the amount of waste material generated is significantly reduced as compared with napkins of the prior art, as graphically illustrated in FIGS. 2 and 5.

Method of Manufacture of Napkins of the Present Invention

FIG. 3 illustrates schematically the various steps in the assembly process of the sanitary napkin. In a first step, there is provided a continuous strip 400 of fluid impervious material which will form the barrier layer of the napkin which has the desired thickness and is of appropriate width. This width is equal to the length of longitudinal centre-line of the articles being manufactured plus any additional width necessary for the handling of the material by the manufacturing apparatus.

In a subsequent step, absorbent cores 402 are serially applied to the continuous web in a spaced apart relationship in the desired position. The position of each absorbent core on the web is selected according to the pattern by which the final products will be severed from the web. The exact application and positioning of the cores along the web may be accomplished by several means including a conveyor belt or vacuum drum.

In a subsequent step, a transfer layer 404 is applied to the absorbent core by a similar means as with the cores. A second continuous strip 406 of fluid-permeable material forming the cover layer of the final articles then applied. This strip will contact the transfer layers disposed along the first web, and the barrier layer strip in areas where no absorbent core/transfer layer is located.

The superposed layers are sealed together at sealing station 408 along the margins of the absorbent cores in a desired pattern to form a continuous compound web. There are a number of methods which may be used to accomplish this task, such as adhesives, heat-sealing, and mechanical crimping, among others. A continuous, laminated, sealed web of material is thus formed. Adhesive strips are then applied (not shown) to the exterior surface of the barrier layer material.

It should be noted that the method described above could be modified to form the sanitary napkins upside down, which involves starting with the cover layer rather than the barrier layer. This variant also requires to change the order of deposition of the transfer layer and the absorbent core, the transfer layer being placed first followed by the absorbent core. Finally, the barrier layer is put in place and the compound web is sealed.

The final step in the process is to sever the individual articles from the continuous, laminated, sealed web of material, at cutting station 410 that uses a die-cutting roll 412. In this respect, individual articles are severed along the dark line appearing in FIG. 5 by die-cutting.

A second aspect of the present invention allows for the manufacture of sanitary absorbent articles having a prior art flap configuration as depicted in FIG. 1 with less waste material generated. This method of manufacture is generally the same as that previously described with respect to the first aspect, except that the absorbent cores/transfer layers are positioned within the web according to the cutting pattern described hereinbelow.

Figure 6:
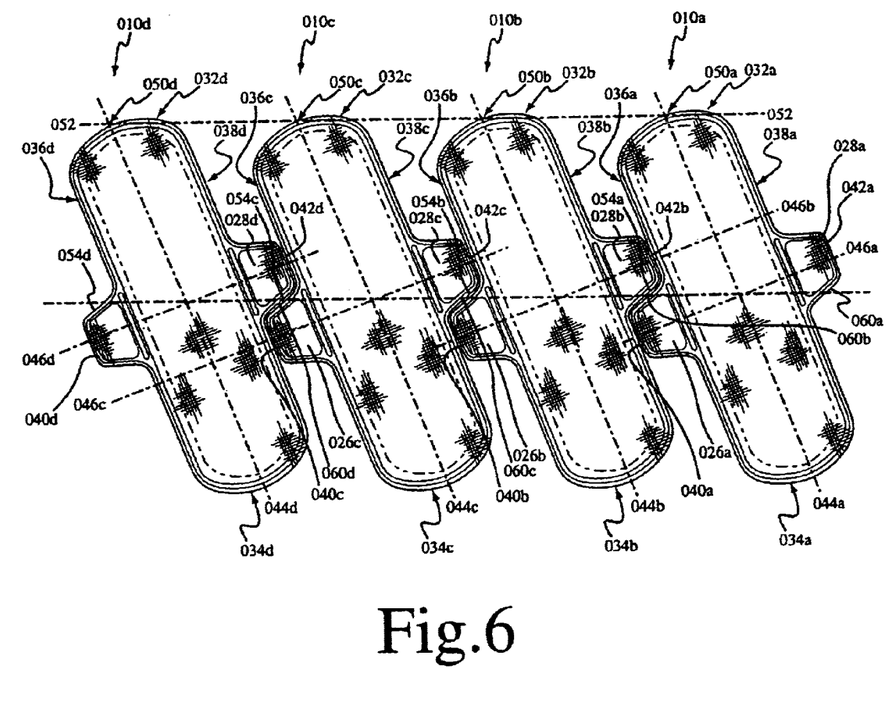
FIG. 6 illustrates a severing pattern of the present invention for the manufacture of the absorbent article, or a component layer thereof, depicted in FIG. 1.

In this configuration, the napkins 010a, 010b, 010c, 010d are positioned side-by-side with successive articles being of the same orientation (i.e. Opposite longitudinal sides of successive napkins face one another. Thus, the first longitudinal side 036a of the first article 010a faces the second longitudinal 038b of the second article 010b and the first longitudinal side 036b of the second article 010b faces the second longitudinal side 038c of the third article 010c.) The points of intersection 050a, 050b, 050c, 050d of like transverse sides 032a, 032b, 032c, 032d of each napkin 010a, 010b, 010c, 010d with the longitudinal centre-line 044a, 044b, 044c, 044d of that napkin are collinear. However, note that line 052 is not parallel to the transverse centre-line 046a, 046b, 046c, 046d of the napkins, nor is that line 052 perpendicular to the longitudinal centre-line 044a, 044b, 044c, 044d of each napkin.

Opposite longitudinal sides of opposite flaps of successive napkins are substantially in contact with one another. Thus, the first longitudinal side 054a of the first flap 026a of the first napkin 010a is substantially in contact with the second longitudinal side 060b of the second flap 028b of the second napkin 010b. Similarly, the first longitudinal side 054b of the first flap 026b of the second napkin 010b is substantially in contact with the second longitudinal side 060c of the second flap 028c of the third napkin 010c. Similarly, the lateral side 040b of the first flap 026b of the second napkin 010b is substantially in contact with the second longitudinal side 038c of the main body 030c of the third napkin 010c, and the lateral side 042c of the second flap 028c of the third napkin 040c is in substantially in contact with the first longitudinal side 036b of the main body 030b of the second napkin 010b.

A third aspect of the present invention also allows for the manufacture of sanitary absorbent articles having a prior art flap configuration is depicted in FIG. 1 with less waste material generated. This method of manufacture is generally the same as those previously described with respect to the first and second aspects, except that once again the absorbent cores/transfer layers are positioned within the web according to the cutting pattern described hereinbelow. In this respect, illustrated in FIG. 7 is the positioning of final articles within the continuous sealed web of the present embodiment, and the cutting pattern therefor.

In this configuration, the napkins 010*a*, 010*b*, 010*c* are positioned side-by-side with successive articles being of the same orientation as the last, however, only a portion of opposite longitudinal sides of successive napkins face one another. Thus, a portion of the first longitudinal side 036*a* of the first article 011*a* faces a portion of the second longitudinal 038*b* of the second article 010*b* and a portion of the first longitudinal side 036*b* of the second article 010*b* faces a portion of the second longitudinal side 038*c* of the third article 010*c*. The points of intersection 050*a*, 050*b*, 050*c* of like transverse sides 032*a*, 032*b*, 032*c* of each napkin 010*a*, 010*b*, 010*c* with the longitudinal centre-line 044*a*, 044*b*, 044*c* of that napkin are collinear. However, note that line 052 is not parallel to the transverse centre-line 046*a*, 046*b*, 046*c* of the napkins, nor is that line 052 perpendicular to the longitudinal centre-line 044*a*, 044*b*, 044*c* of each napkin.

Figure 7:
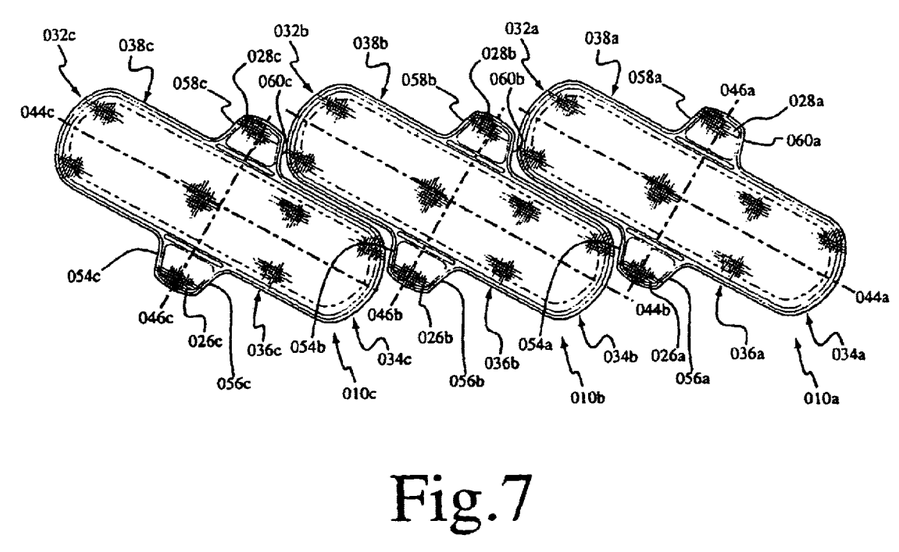
FIG. 7 illustrates a severing pattern of the present invention for the manufacture of absorbent articles or component layers thereof, in accordance with a variant.
Figure 8:
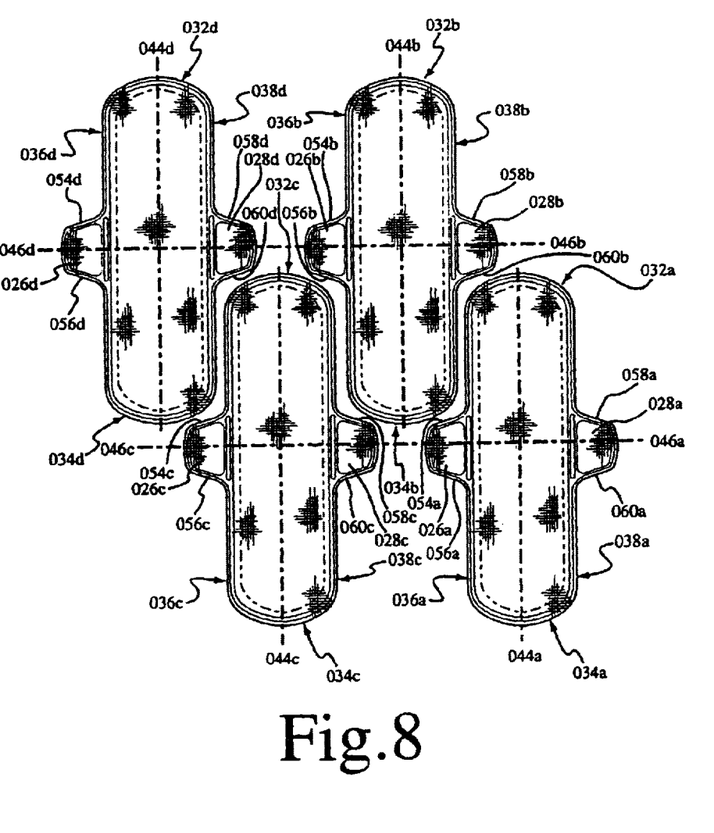

As is illustrated in FIG. 7, it is preferred that the contacting portions of the longitudinal sides of successive articles be substantially in contact with one another in order to minimize waste material generated.

The above description of a preferred embodiment should not be interpreted in any limiting manner since variations and refinements are possible which are within the spirit and scope of the present invention. The scope of the invention is defined in the appended claims and their equivalents.

What is claimed is:

1. A method of manufacturing sanitary absorbent articles suitable for placement within a crotch portion of an undergarment of a wearer, each article comprising:

i) a main body, the main body having a first transverse side, a second transverse side, a first longitudinal side, a second longitudinal side, and an imaginary longitudinal center-line; and ii) a first flap capable of being folded about a first side edge of the crotch portion of the wearer's undergarment when the article is in use by the wearer, the first flap projecting laterally from the first longitudinal side of the main body, the first flap having to longitudinal sides, each longitudinal side projecting laterally outward from the first longitudinal side of said main body intermediate the transverse sides of said main body;

comprising the steps of:

A) providing a web of at least one layer of continuous material;

B) severing from the web a first article and a second article arranged on with respect to the other such that:

(1) the second article is rotated with respect to the first article such that the first longitudinal side of the main body of each of the articles faces the first longitudinal side of the main body of the other of the articles, and (2) the first transverse side of each of the articles is aligned with the second transverse side of the other of the articles, and (3) an imaginary line generally parallel to, and located in-between, the longitudinal center-lines of each of the main bodies of each of the articles simultaneously intersects the first flap of each of the articles and wherein the second article is severed from the web arranged with respect to the first article such that one of the longitudinal sides of the first flap of the second article is substantially in contact with one of the longitudinal sides of the first flap of the first article.

* * * * *